United States Patent [19]

LaFuente

[11] 4,332,039
[45] Jun. 1, 1982

[54] OCULAR PROSTHESIS WHICH SIMULATES CHANGE IN PUPIL DIAMETER

[76] Inventor: Henry LaFuente, 608 Stanton L. Young Blvd., Oklahoma City, Okla. 73104

[21] Appl. No.: 202,699

[22] Filed: Oct. 31, 1980

[51] Int. Cl.³ .............................................. A61F 1/16
[52] U.S. Cl. ............................................ 3/13; 46/165
[58] Field of Search ................................ 3/13; 46/165

[56] References Cited

U.S. PATENT DOCUMENTS 3,480,971 12/1969 Smith ........................................ 3/13
4,272,910 6/1981 Danz ..................................... 3/13 X Primary Examiner—Clifford D. Crowder
Attorney, Agent, or Firm—Dunlap & Codding

[57] ABSTRACT

An improved ocular prosthesis is provided in which the diameter of the pupil of the prosthesis can readily be varied to correspond to the diameter of the pupil of a person's natural eye when same is exposed to either direct or indirect light. The ocular prosthesis comprises a body portion having an anterior surface, a spatially disposed posterior surface, and a channel formed therebetween; an iris forming member secured to the anterior surface of the body portion, the iris forming member having a transparent central portion with a diameter substantially corresponding in size to the diameter of the pupil of the natural eye when same is exposed to indirect light, an outer iris colored portion, and a pupil colored area selectively positioned in the transparent central portion, the pupil colored area substantially corresponding in diameter to the diameter of the pupil of the natural eye when same is exposed to direct light; a pupil colored surface forming member disposed within the body portion between the posterior surface of the body portion and the channel such that the pupil colored surface member is substantially adjacent the channel and at least a portion of the pupil colored surface forming member is aligned with the transparent central portion of the iris forming member; and an iris colored member positioned within the channel of the body portion, the iris colored member being selectively movable between a first position in which the iris colored member is in a non-interposing relationship between the transparent central portion of the iris forming member and the pupil colored surface member and a second position wherein the iris colored member is interposed between the transparent central portion of the iris forming member and the pupil colored surface forming member.

12 Claims, 9 Drawing Figures

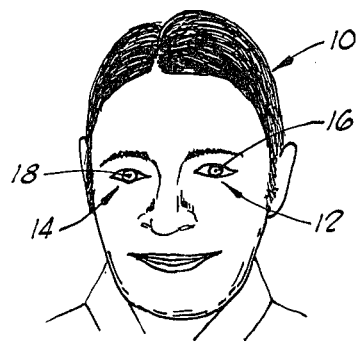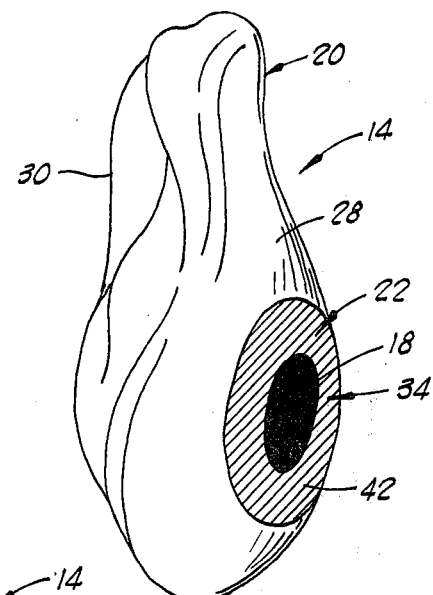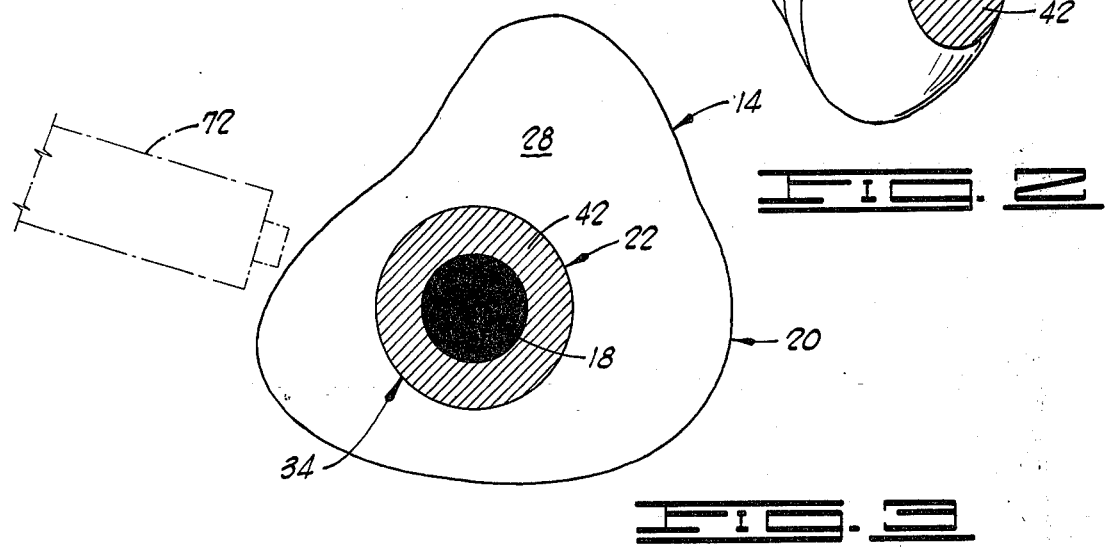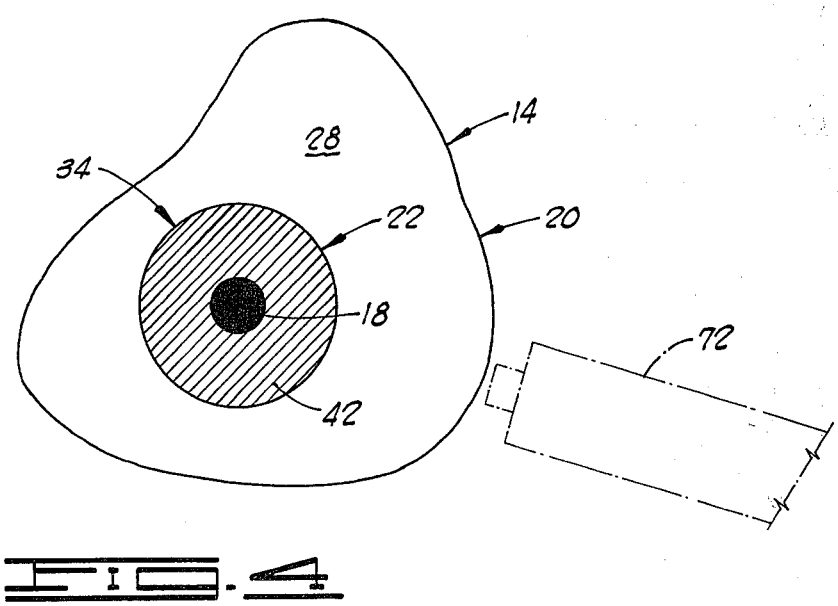

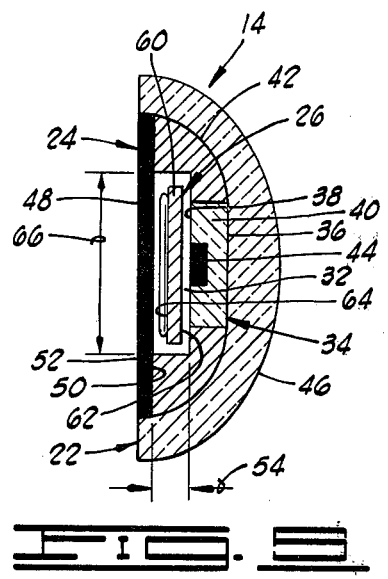
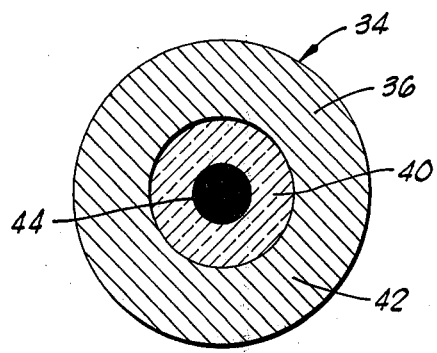
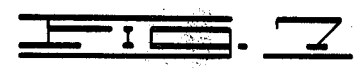
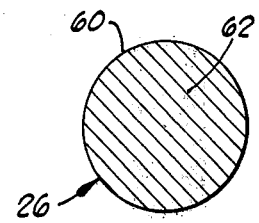
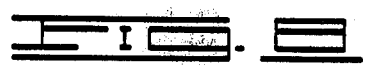
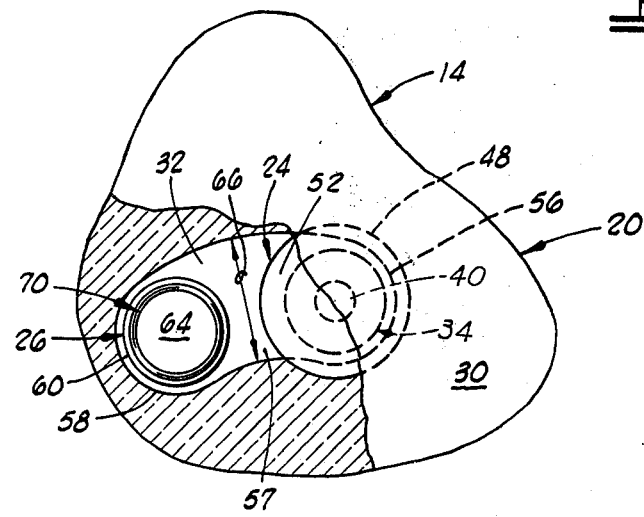
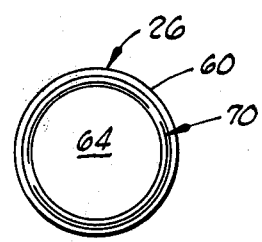
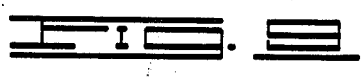
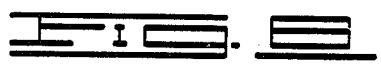

OCULAR PROSTHESIS WHICH SIMULATES CHANGE IN PUPIL DIAMETER

BACKGROUND OF THE INVENTION

1. Field of the Invention

The present invention relates generally to an ocular prosthesis, and more particularly, but not by way of limitation, to an ocular prosthesis wherein the pupil diameter of the prosthesis may be varied depending upon light intensity.

2. Brief Description of the Prior Art

Ocular prosthesis have heretofore been utilized as a cosmetic replacement for an enucleated or eviscerated eye. Ocular prosthesis are generally constructed from colored methyl methacrylate resin and are provided with an iris having a pupil with a fixed diameter. Thus, the pupil diameter of such ocular prosthesis may or may not be compatible with the natural eye of the person depending upon the light intensity.

It is highly desirable that the ocular prosthesis provide a natural-looking appearance so that the wearer of the ocular prosthesis does not feel conspicuous. In order for such to occur it is highly desirable that some means be provided for varying the pupil diameter of the ocular prosthesis to correspond to the diameter of the pupil of the natural eye when the natural eye is exposed to indirect light and direct light. Such is especially important if one is to provide an ocular prosthesis with functions in appearance as close as possible to that of the persons's natural eye.

SUMMARY OF THE INVENTION

An object of the present invention is to provide an ocular prosthesis in which the pupil diameter of the prosthesis can be varied to simulate the pupil diameter of a natural eye depending upon light intensity to which the natural eye is exposed.

Another object of the present invention is to provide an ocular prosthesis in which the pupil diameter of the prosthesis can be varied to simulate a natural eye by the person having the ocular prosthesis depending upon the light intensity to which the person's natural eye is exposed.

Another object of the present invention is to provide an ocular prosthesis in which the pupil diameter can be varied, which is economical to manufacture, substantially troublefree in operation, and which simulates the natural eye of the person wearing the ocular prosthesis.

These and other objects, advantages, and features of the present invention will be apparent to those skilled in the art from a reading from the following detailed description when read in conjunction with the drawings which accompany this disclosure and with the appended claims.

According to the present invention an improved ocular prosthesis is provided in which the diameter of the pupil of the prosthesis can be varied to substantially correspond to the diameter size of the pupil of a person's natural eye when same is exposed to either direct or indirect light. The improved ocular prosthesis comprises a body portion, an iris forming member, an internally disposed movable iris colored member, and a pupil colored surface forming member. The body portion of the ocular prosthesis is provided with an anterior surface, a spatially disposed posterior surface, and a channel formed therebetween. The iris forming member is disposed on the anterior surface of the body portion and the iris forming member is provided with a transparent central portion, and outer iris colored portion, and a pupil colored area selectively positioned in the transparent central portion. The transparent central portion of the iris forming member is provided with a diameter substantially corresponding to the diameter of the pupil of the person's natural eye when same is exposed to indirect light; and the pupil colored area of the iris forming member is provided with a diameter substantially corresponding to the diameter of the pupil of the person's natural eye when same is exposed to direct light.

The pupil colored surface forming member is disposed within the body portion of the ocular prosthesis at a position between the posterior surface and the channel such that the pupil colored surface forming member is substantially adjacent the channel and at least a portion of the pupil colored surface forming member is aligned with the transparent central portion of the iris forming member. The iris colored member is positioned within the channel of the body portion of the ocular prosthesis and is selectively movable between a first position wherein the iris colored member is in a non-interposing position between the transparent central portion of the iris forming member and the pupil colored surface forming member, and a second position wherein the iris colored member is interposed between the transparent central portion of the iris forming member and the pupil colored surface forming member. The body portion of the ocular prosthesis is provided with a configuration substantially corresponding to the orbital soft tissue of an eye socket, and the channel containing the iris colored member is filled with a transparent, free-flowing fluid which stabilizes the iris colored member in one of the first and second positions and provides substantially friction-free movement of the iris colored member between one of the first and second positions.

BRIEF DESCRIPTION OF THE DRAWINGS

FIG. 1 is a facial view of a person having an ocular prosthesis constructed in accordance with the present invention.

FIG. 2 is an enlarged, prospective view of the ocular prosthesis of the present invention wherein the body portion of the ocular prosthesis is provided with a configuration substantially corresponding to the orbital soft tissue of an eye socket.

FIG. 3 is a front elevational view of the ocular prosthesis of the present invention wherein the diameter of the pupil of the ocular prosthesis is adjusted to simulate the diameter of the pupil of the natural eye when same is exposed to indirect light, and illustrating, in phantom, a magnetic element for selectively changing the diameter of the pupil of the ocular prosthesis.

FIG. 4 is a front elevational view of an ocular prosthesis constructed in accordance with the present invention wherein the diameter of the pupil of the ocular prosthesis is adjusted to simulate the diameter of the pupil of the natural eye when same is exposed to direct light, and illustrating, in phantom, a magnetic element for selectively changing the diameter of the pupil of the ocular prosthesis.

FIG. 5 is a partially broken, cross-sectional view of the ocular prosthesis of the present invention.

FIG. 6 is a partial cutaway rear elevational view of the ocular prosthesis of the present invention illustrating the channel formed in the body portion of the ocular prosthesis, the iris colored member positioned within the channel, and the pupil colored member.

FIG. 7 is a front plan view of the iris forming member of the ocular prosthesis of the present invention.

FIG. 8 is a front plan view of the iris colored member of the ocular prosthesis of the present invention.

FIG. 9 is a rear elevational view of the iris colored member of the ocular prosthesis constructed in accordance with the present invention.

DETAILED DESCRIPTION OF PREFERRED EMBODIMENTS

Referring now to the drawings, and particularly to FIG. 1, a person 10 is illustrated having a natural eye 12 and an ocular prosthesis 14 constructed in accordance with the present invention. The natural eye 12 includes a pupil 16, and the ocular prosthesis 14 includes a pupil 18. The ocular prosthesis 14 is constructed such that the person 10 can vary the diameter of the pupil 18 of the ocular prosthesis 14 to substantially correspond to the diameter of the pupil 16 of the natural eye 12 when the natural eye 12 is exposed to direct light or indirect light.

As more clearly illustrated in FIGS. 2–6, the ocular prosthesis 14 comprises a body portion 20, an iris forming member 22, a pupil colored surface forming member 24, and an iris colored member 26. The body portion 20 of the ocular prosthesis 14 is provided with an anterior surface 28, a spatially disposed posterior surface 30, and a channel 32 formed therebetween. The body portion 20 of the ocular prosthesis 14 is provided with a configuration substantially corresponding to the orbital soft tissue of an eye socket (not shown) so that the ocular prosthesis 14 can readily be placed in a natural appearing position in the eye socket. The body portion 20 of the ocular prosthesis 14 can be fabricated of any suitable material well known in the art of ocular prosthesis, such as a scleral colored methyl methacrylate resin.

The iris forming member 22 of the ocular prosthesis 14 is disposed on the anterior surface 28 of the body portion 20 at a predetermined position to simulate the iris location of the person's natural eye. As more clearly illustrated in FIGS. 5 and 7, the iris forming member 22 comprises a corneal button 34 having an anterior side 36 and a spatially disposed posterior side 38. The corneal button 34 is further characterized as having a transparent central portion 40, an outer iris colored portion 42, and a pupil colored area 44 selectively positioned in the transparent central portion 40. The transparent central portion 40 of the corneal button 34, a substantially circular shaped portion, is provided with a diameter substantially corresponding to the diameter of the pupil 16 of the natural eye 12 when the natural eye 12 is disposed to indirect light. On the other hand, the pupil colored area 44 of the corneal button 34, a substantially circular shaped area centrally disposed within the transparent central portion 40 of the corneal button 34, has a diameter substantially corresponding to the diameter of the pupil 16 of the natural eye 12 when the natural eye 12 is exposed to direct light.

In order to provide the iris colored portion 42 of the corneal button 34 with an appearance substantially corresponding to the color of the iris of the natural eye 12, the anterior side 36 of the corneal button 34 defining the iris colored portion 42 is tinted with an admixture of selected earth pigments and monopoly so that the iris colored portion 42 of the corneal button 34 matches the color of the iris of the natural eye 12. As is well known to those skilled in the art of ocular prosthesis monopoly is a viscous liquid made from one part methyl methacrylate polymer and ten parts methyl methacrylate monomer.

To provide the anterior side 36 of the corneal button 34 with a desired curvature and depth appearance so that the corneal button 34 simulates the iris of the natural eye 12, the anterior surface 36 of the corneal button 34 is modified by coating same with clear resin to provide a covering 46 as illustrated in FIG. 5. The use of the clear resin to form the covering 46 over the anterior side 36 of the corneal button 34 provides the corneal button 34 with the beforementioned contour corresponding to the iris of the natural eye 12, while at the same time providing the anterior side 36 of the corneal button 34 with the desired visual depth. Further, by covering the anterior side 36 of the corneal button 34 with the clear resin to form the covering 46, the anterior side 36 of the corneal button 34 is provided with surface protection. Any suitable clear resin can be employed to form the covering 46 on the anterior surface 36 of the corneal button 34. However, desirable results have been obtained where the resin employed to coat the anterior surface 36 of the corneal button 34 is a clear methyl methacrylate resin marketed by Esschem Company, P.O. Box 56, Essington, Pa. 19029 under the trade name Polymer Type 12, Clear 012E0000.

Referring again to FIGS. 5 and 6 the pupil colored surface forming member 24 of the ocular prosthesis 14 comprises a pupil colored disc 48 having a first side 50 and an opposed second side 52. The disc 48, which is of the same color as the pupil colored area 44 of the corneal button 34 (i.e. black) is positioned within the body portion 20 of the ocular prosthesis 14 so as to be disposed a distance 54 from the posterior side 38 of the corneal button 34. Thus, the first side 50 of the disc 48 and the posterior side 38 of the corneal button 34 define a first end portion 56 of the channel 32 in the body portion 20 of the ocular prosthesis 14, and the first end portion 56 of the channel 32 is disposed between the transparent central portion 40 of the corneal button 34 and the disc 48.

As more clearly illustrated in FIG. 6 the channel 32, an elongated, laterally extending channel preferably having a configuration as shown, is provided with the first end portion 56, a medial portion 57, and a second end portion 58. The channel 32 is adapted to receive the iris colored member 26 such that the iris colored member 26 can be selectively moved through the channel 32 from the first end portion 56 to the second end portion 58, and visa versa. Further, the curvature of the medial portion 57 of the channel 32 assists in stabilizing the iris colored member 26 in one of the first or second positions.

When the iris colored member 26 has been selectively moved to the first end portion 56 of the channel 32 the iris colored member 26 is interposed between the transparent central portion 40 of the corneal button 34 and the pupil colored disc 48. Thus, the pupil 18 of the ocular prosthesis 14 appears to have a diameter substantially corresponding to the diameter of the pupil 16 of the natural eye 12 when same is exposed to direct light. On the other hand, when the iris colored member 26 is moved to the second end portion 58 of the channel 32 the iris colored member 26 is in a non-interposing relationship with the transparent central portion 40 of the corneal button 34 and the pupil colored disc 48. Thus, the pupil 18 of the ocular prosthesis 14 is provided with a diameter substantially corresponding to the diameter of the pupil 16 of the natural eye 12 when same is exposed to indirect light.

As heretofore setforth, the posterior side 38 of the corneal button 34 and the first side 50 of the disc 48 define the first end portion 56 of the channel 32 positioned therebetween. However, it should be noted that the channel 32 in the body portion 20 of the ocular prosthesis 14 is a fluid-tight channel for reasons which will be setforth hereinafter.

As previously stated the iris colored member 26 is positioned within the channel 32 and movable between the first end portion 56 and the second end portion 58. The selective movement of the iris colored member 26 through the channel 32 is more clearly illustrated in FIGS. 5 and 6.

Referring now to FIGS. 5, 6, 8 and 9, the iris colored member 26 comprises a disc 60 having a first side 62 and an opposed second side 64. The disc 60 is tinted on at least its first side 62 with an admixture of the selected earth pigments and monopoly to substantially match the color of iris colored portion 42 of the corneal button 34. The disc 60 is freely movable within the channel 32 between the first end portion 56 and the second end portion 58 such that the disc 60 can be selectively moved between one of the first position (a non-interposing relationship between the corneal button 34 and the disc 48) and the second position (wherein the disc 60 is interposed between the transparent central portion 40 of the corneal button 34 and the disc 48).

The disc 60 is maintained in the channel 32 in a substantially upright position because of the dimensions of the channel 32 and the disc 60. While the dimensions of the channel 32 and the disc 60 can vary widely, desirable results have been obtained where the channel 32 was provided with a height 66 at least about twenty-five percent greater than the diameter of the disc 60, and the width of the channel 32 (which corresponds to the distance 54 between the posterior side 38 of the corneal button 34 and the first side 50 of the disc 48) is substantially twice the thickness of the disc 60. By providing the channel 32 and the disc 60 with the proper dimensions the disc 60 is maintained in a substantially upright position when the disc is in one of the first and second position, or during movement of the disc 60 through the medial portion 57 of the channel 32.

In order to further stabilize the disc 60 of the iris colored member 26 in the upright position, when same is in one of the first or second positions as well as during the movement through the medial portion 57 of the channel 32, the channel 32 (a fluid-tight channel) is filled with a transparent, free-flowing fluid, such as a low molecular weight silicone. The transparent, free-flowing fluid, in addition to stabilizing the disc 60 of the iris colored member 26 in the channel 32, further insures a substantially friction-free movement of the disc 60 through the channel 32. While any suitable transparent, free-flowing fluid can be employed in the channel 32 especially desirable results have been obtained when the transparent, free-flowing fluid is a low viscosity silicone marketed by Hansen Ophthalmic Development Laboratory, P.O. Box 613, Iowa City, Iowa 52240, under the trade name "Sil-OPHTHO".

In order to allow for the selective movement of the disc 60 through the medial portion 57 of the channel 32 so that the disc 60 can be positioned in one of the first position or the second position as heretofore described, a ferro-magnetic element 70 is secured to the second side 64 of the disc 60 so that magnetic properties can be imparted to the disc and the disc can be selectively moved between one of the first and second positions by a magnet 72 positioned exterior the ocular prosthesis 14 as indicated by phantom lines in FIGS. 3 and 4. While any suitable ferro-magnetic material can be employed to impart the desired magnetic properties to the disc 60, desirable results have been obtained when the ferro-magnetic element 70 is a 32 gauge orthodonic wire and the orthodonic wire is disposed around the perimeter of the disc 60 and secured to the second side 64 of the disc 60 substantially as shown in FIG. 9. It should be noted that in order to provide free movement of the disc 60 through the channel 32 of the ocular prosthesis 14 the width of the channel 32 is greater than the combined width of the disc 60 and the ferro-magnetic element 70, such as the orthodonic wire.

The ocular prosthesis 14 described above enables the person 10 to vary the diameter of the pupil 18 of the ocular prosthesis 14 by selectively positioning the magnet 72 so as to cause the desired movement of the disc 60 to either the first end portion 56 of the channel 32 (wherein the disc 60 of the iris colored member 26 in the second or interposing position); or to the second end portion 58 of the channel 32 (wherein the disc 60 of the iris colored member 26 is in the first or non-interposing position).

It should be noted that the changing of the diameter of the pupil 18 of the ocular prosthesis 14 can be accomplished with substantially no attention being drawn to the person 10. Further, any suitable method can be employed to fabricate the ocular prosthesis 14 of the present invention.

To assist in a better understudy of the various components of the ocular prosthesis 14 and the interrelationship of the various components, the following procedure is setforth. However, it is to be understood that the following technique for fabricating the ocular prosthesis 14 of the present invention is for illustration purposes only and is not to be construed as limiting the ocular prosthesis of the present invention.

To fabricate the ocular prosthesis 14 described above one first makes a mold for use in forming the ocular prosthesis. Initially an impression of the ocular defect is made and a custom wax conformer is constructed according to the techniques of Allen. Once the wax conformer has been constructed an iris disc of appropriate diameter is selected and tinted with an admixture of selected dry earth pigments and monopoly to provide the iris disc with a color substantially corresponding to the color of the iris of the natural eye. Thereafter, a corneal button having a pupil diameter substantially corresponding to the pupil diameter 16 of the natural eye 12 when same is exposed to direct light is attached to the tinted iris disc with monopoly. The corneal button is then positioned in the wax conformer to simulate the iris location in the natural eye 12. At this point the wax conformer is modified externally to provide the wax conformer with the optimum orbital soft tissue contour of the eye socket into which the ocular prosthesis 14 is to be placed. The modified wax conformer is then positioned in a metal flask containing improved stone (dental plaster). Once the improved stone (dental plaster) has set the flask is opened and the modified wax conformer and the attached corneal button are removed, thus providing a mold for the ocular prosthesis.

Once the appropriate mold has been formed two blank iris discs having the same diameter as the iris disc employed in the formation of the mold, are attached to the posterior side 38 of a corneal button 34 with autopolymerizing methyl methacrylate at a plurality of points around the periphery of the discs. The corneal button 34, a clear button which is a duplicate of the corneal button employed in the formation of the mold, is provided with the centrally disposed pupil colored area 44. The corneal button 44, having the two blank iris discs attached to the posterior side 38, is then positioned in the mold and processed with scleral colored methyl methacrylate (Polymer Type 12, I.B. White 012E3007 marketed by Esschem Company, P.O. Box 56, Essington, Pa. 19029) to form the body portion 20 of the ocular prosthesis 14. Once the body portion 20 of the ocular prosthesis 14 has been formed, the cured prosthesis is removed from the mold and the anterior side 36 of the corneal button 34 is ground to within about one-half millimeter of the iris disc, taking care to insure that the pupil colored area 44 remains.

The pupil colored area 44 of the corneal button 34, substantially corresponds in diameter to the diameter of the pupil 16 of the natural eye 12 when the natural eye 12 is exposed to direct light. However, since it is desirable to enable the pupil 18 of the ocular prosthesis 14 to be varied to correspond to the diameter of the pupil 16 of the natural eye 12 when same is exposed to indirect light, one first observes the diameter of the pupil 16 of the natural eye 12 when same is exposed to indirect light and measures the diameter of pupil 16 under such a condition. Thereafter, a circle is scribed on the anterior side 36 of the corneal button 34 such that the pupil colored area 44 of the corneal button 34 is centrally disposed in the scribed circle. Further, the scribed circle is of the same diameter as that determined for the pupil 16 of the natural eye 12 when same is exposed to indirect light.

The portion of the anterior side 36 of the corneal button 34 located between the scribed circle and the outer perimeter of the corneal button 34 is then tinted with an admixture of selected earth pigments and monopoly to provide the iris colored portion 42 of the corneal button 34 substantially corresponding in color to the iris colored portion of the natural eye 12. In order to insure that the body portion 20 of the ocular prosthesis 14 is as similar to the natural eye 12 as possible the scleral colored methyl methacrylate body portion 20 of the prosthesis 14 is tinted with selected earth pigments to substantially match the fibrous white outer coating of the natural eye 12.

The ocular prosthesis 14 is again positioned in the mold and processed in clear methyl methacrylate (Polymer Type 12, Clear 012E0000 marketed by Esschem Company, P.O. Box 56, Essington, Pa. 19029) to provide the covering 46 over the anterior side 36 of the corneal button 34 and thereby provide the anterior side 36 of the corneal button with the desired contour, visual depth and surface protection. After the ocular prosthesis 14 has been cured the prosthesis is removed from the mold and an opening is formed in the body portion 20 of the prosthesis 14 via the posterior surface 30 thereof so that the two iris discs previously attached to the posterior side 38 of the corneal button 34 are exposed. The two iris discs, which were detachably secured to the posterior side 38 of the corneal button 34, are thereafter removed and a slot is cut in the body portion 20 of the ocular prosthesis 14 via the posterior surface 30 thereof so that the slot extends toward the lateral margin of the body portion 20. The sides of the opening formed in the body portion 20 for the removal of the two iris discs, as well as the slot formed in the body portion 20, are beveled to remove any undercuts.

Two iris discs of an identical diameter to those removed from the opening out in the body portion 20 of the ocular prosthesis 14 are then positioned in the opening formed in the body portion 20 of the ocular prosthesis 14. The beveled edges of the opening, as well as the laterally extending slot, are lubricated with vaseline and liquid wax is positioned on top of the two discs so that the wax is to within about 1 millimeter of the posterior surface 30 of the body portion 20 of the ocular prosthesis 14. After the wax has set, the wax plug is removed along with one iris disc which will be attached to the wax. The wax plug and attached iris disc are thereafter employed to make a mold for a methyl methacrylate plug which has the disc 48 attached thereto. The plug, except for the first side 50 of the disc 48, is scleral colored to substantially correspond to the remainder of the body portion 20 of the ocular prosthesis 14. The first side 50 of the disc 48 is, as previously setforth, the same color as the pupil colored area 44 of the corneal button 34.

The iris disc remaining in the opening formed in the body portion 20 of the ocular prosthesis 14 is thereafter removed and reduced in diameter an effective amount to facilitate movement of the disc throughout the channel 32 formed in the body portion 20 of the ocular prosthesis 14 by the opening and the laterally extending slot. Generally it is sufficient if the disc is reduced in diameter by about twenty-five percent by trimming with any suitable means, such as scissors.

In order to impart the desired magnetic properties to the disc 60 having the reduced diameter as prepared above, a ferro-magnetic element 70, such as a 32 gauge orthrodonic wire, is positioned around the perimeter of the disc 60 and secured thereto via the second side 64 of the disc 60. The ferro-magnetic element 70 can be secured to the disc 60 by heating the element 70 and placing the iris disc 60 on top of the heated element 70 whereupon the heat of the element 70 will cause the element 70 to fuse to the iris disc 60. The disc 60 is thereafter coated with an admixture of selected earth pigment and monopoly so that at least the first side 62 of the iris disc 60 is colored to substantially correspond in color to the iris colored portion 42 of the corneal button 34 and the color of the iris of the natural eye 12.

The lateral slot and the opening formed in the body portion 20 of the ocular prosthesis 14 are wider than the width or thickness of the iris colored disc 60. The width of the lateral slot and the opening can be enlarged by undercutting a portion of the posterior surface 30 of the body portion 20 of the ocular prosthesis 14 defining the lateral slot and the opening therein. Desirable results have been obtained when the width of the slot and opening, which define the width of the channel 32, is about twenty-five percent greater than the width or thickness of the iris colored disc 60.

Once the slot and opening have been undercut to provide for free movement of the iris colored disc 60 therethrough, and the iris colored disc positioned therein, the plug containing the disc 48 is positioned in the opening and slot formed on the posterior portion 30 of the body portion 20 such that the channel 32 is formed in the body portion 20. The plug is then sealed in place. However, in order to stabilize the iris colored disc 60 when the disc is selectively positioned in one of the first and second positions, as well as during the movement of the disc 60 through the channel 32 formed in the body portion 20 of the ocular prosthesis 14, a stabilizing fluid is injected into the channel 32 prior to completely sealing the plug. Such can be accomplished by sealing the methyl methacrylate plug having the disc 48 attached thereof in the opening on the posterior surface of the body portion of the prosthesis, except for a pin-hole opening through which a syringe can be placed so that the chamber channel 32 can be filled with a suitable transparent, free-flowing fluid. Thereafter, the pin-hole is sealed to insure that the channel 32 is completely sealed and fluid-tight. Once the channel 32 has been completely sealed, the posterior surface 30 of the ocular prosthesis 14 is ground down to remove approximately one millimeter of the posterior surface 30 of the ocular prosthesis 14, the prosthesis 14 is processed with scleral colored methyl methacrylate and polished to provide the final product.

While the improved ocular prosthesis of the present invention has been described, as well as a particular method for its preparation and typical materials, it should be noted that such an ocular prosthesis can be fabricated in various ways, using varying sizes of materials and compositions. Further, it is clear that the present invention is well adapted to carry out the objects and obtain the ends and advantages mentioned as well as those adherent therein. While a presently preferred embodiment of the invention has been described for purposes of this disclosure, numerous changes may be made which will readily suggest themselves to those skilled in the art and which are encompassed within the spirit of the invention disclosed and as defined in the following claims.

What is claimed is:

1. An improved ocular prosthesis comprising:
    a body portion having an anterior surface, a spatially disposed posterior surface, and a channel formed therebetween;
    iris forming means disposed on the anterior surface of the body portion, the iris forming means having a transparent central portion, an outer iris colored portion, and a pupil colored area selectively positioned in the transparent central portion, the transparent central portion substantially corresponding in size to a pupil of a natural eye when same is exposed to indirect light, the pupil colored area substantially corresponding in size to the pupil of the natural eye when same is exposed to direct light;
    pupil colored surface forming means disposed within the body portion between the posterior surface of the body portion and the channel such that the pupil colored surface forming means is substantially adjacent the channel and at least a portion of the pupil colored surface forming area is aligned with the transparent central portion of the iris forming means; and
    an iris colored member positioned within the channel of the body portion and selectively movable between a first position and a second position, in the first position the iris colored member being in a non-interposing relationship between the transparent central portion of the iris forming means and the pupil colored surface forming means, in the second position the iris colored member being interposed between the transparent central portion of the iris forming means and the pupil colored surface forming means.

2. The improved ocular prosthesis of claim 1 wherein the body portion has a configuration substantially corresponding to the orbital soft tissue of an eye socket.

3. The improved ocular prosthesis of claim 2 wherein the iris forming means and the anterior surface of the body portion surrounding the iris forming means are provided with a convex surface substantially corresponding to the surface of a natural eye.

4. The improved ocular prosthesis of claim 1 wherein the iris forming means comprises a corneal button having an anterior side and a spatially disposed posterior side, the anterior surface being covered with an effective amount of a transparent polymeric material to provide the desired convex surface and provide a desired visual depth thereto.

5. The improved ocular prosthesis of claim 4 wherein the pupil colored area is a substantially circularly shaped black area, and the pupil colored surface forming means is a black disc.

6. The ocular prosthesis of claim 5 wherein the black disc forms one side portion of the channel and at least a portion of the posterior side of the corneal button forms a spatially disposed second side portion of the channel.

7. The ocular prosthesis of claim 1 wherein the iris colored member is a disc having a first side and a second side, at least the first side of the disc being colored to substantially correspond to the color of the outer iris colored portion of the iris forming means.

8. The ocular prosthesis of claim 1 which further comprises a transparent, free-flowing fluid disposed within the channel for stabilizing the iris colored member in one of the first and second positions and for substantially friction-free movement of the iris colored member as the iris colored member is selectively moved through the channel between one of the first and second positions.

9. The ocular prosthesis of claim 8 wherein the transparent, free-flowing fluid is a low molecular weight silicone.

10. The ocular prosthesis of claim 1 wherein the iris colored member comprises:
    a disc having a first side and an second side, the first side of the disc being disposed in a facing relationship with the anterior surface of the body portion; and
    ferro-magnetic means for imparting magnetic properties to the disc such that the disc can be selectively moved between one of the first and second position via a magnet.

11. The ocular prosthesis of claim 10 wherein the ferro-magnetic means comprises a ferro-magnetic element secured to the opposed second side of the disc.

12. The ocular prosthesis of claim 11 wherein the ferro-magnetic element comprises an orthodonic wire ring secured to the second side of the disc such that the wire ring is substantially adjacent the perimeter of the disc.

* * * * *